United States Patent
Yamaguchi et al.

(10) Patent No.: US 11,807,740 B2
(45) Date of Patent: Nov. 7, 2023

(54) METHOD FOR DETERMINING WHETHER OR NOT TEST SAMPLE CONTAINS PHYTOPATHOGENIC FUNGUS

(71) Applicant: Panasonic Intellectual Property Management Co., Ltd., Osaka (JP)

(72) Inventors: Kaori Yamaguchi, Fukui (JP); Yoshitsugu Uriu, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 196 days.

(21) Appl. No.: 17/378,468

(22) Filed: Jul. 16, 2021

(65) Prior Publication Data
US 2021/0340589 A1  Nov. 4, 2021

Related U.S. Application Data

(60) Division of application No. 16/162,467, filed on Oct. 17, 2018, now Pat. No. 11,098,340, which is a continuation of application No. PCT/JP2016/004417, filed on Sep. 30, 2016.

(30) Foreign Application Priority Data

Jul. 15, 2016 (JP) ................. 2016-139916

(51) Int. Cl.
 C08L 1/02 (2006.01)
 C12Q 1/04 (2006.01)
 C12M 1/12 (2006.01)
 C12N 1/14 (2006.01)

(52) U.S. Cl.
 CPC ............ C08L 1/02 (2013.01); C12M 25/06 (2013.01); C12N 1/14 (2013.01); C12Q 1/04 (2013.01)

(58) Field of Classification Search
 None
 See application file for complete search history.

(56) References Cited

U.S. PATENT DOCUMENTS

| 9,410,210 B2 | 8/2016 | Mach et al. |
| 2013/0071356 A1 | 3/2013 | Galiana et al. |

FOREIGN PATENT DOCUMENTS

| EP | 1400366 A2 | 3/2004 | |
| EP | 3128001 | 2/2017 | |
| JP | 2005-287337 A | 10/2005 | |
| WO | WO-2004018623 A2 * | 3/2004 | ......... G01N 21/6428 |
| WO | 2011/090802 A1 | 7/2011 | |

OTHER PUBLICATIONS

Millipore, "Cell Culture Solutions: Millicell® Inserts & Sterile Filtration" product selection guide; Millipore Corporation: Billerica, MA; pp. 1-16 (Year: 2008).*
The Extended European Search Report dated Feb. 5, 2019 for the related European Patent Application No. 16908739.2.
Z. Zhang et al., Molecular detection of *Fusarium oxysporum f.* sp. niveum and Mycosphaerella melon is in infected plant tissues and soil, 2005, FEMS Microbiology Letters 249: 39-47 (Year: 2005).
X. Cao et al, Structure and properties of cellulose films coated with polyurethane/benzyl starch semi-IPN coating, 2006, Ind. Eng. Chem. Res. 45: 4193-4199 (Year: 2006).
Biology definition of pore from Academic Press Dictionary of Science and Technology (Year: 1996).
De Rossi et al "Semi-selective culture medium for Exserohilum turcicum isolation from corn seeds," Summa Phytopathol. vol. 40, No. 2, p. 163-167 (Year: 2014).
Extended European Search Report dated Nov. 21, 2019 for trhe related European Patent Application No. 16908739.2.
International Search Report of PCT application No. PCT/JP2016/004417 dated Dec. 27, 2016.
Paul F. Morris et al., "Chemotropic and Contact Responses of Phytophthora sojae Hyphae to Soybean Isoflavonoids and Artificial Substrates," Plant Physiol (1998) 117:1171-1178 (Published on Aug. 1, 1998).
Non-Final Office Action issued in related U.S. Appl. No. 16/162,467, dated Jul. 23, 2020.
Final Office Action issued in related U.S. Appl. No. 16/162,467, dated Dec. 30, 2020.
Notice of Allowance issued in related U.S. Appl. No. 16/162,467, dated Apr. 21, 2021.

* cited by examiner

*Primary Examiner* — Michelle F. Paguio Frising
(74) *Attorney, Agent, or Firm* — McDermott Will & Emery LLP

(57) ABSTRACT

The present invention provides a method for determining whether or not a test sample contains a phytopathogenic fungi selectively from two kinds of fungi of a phytopathogenic fungus and a non-phytopathogenic fungus. The method according to the present invention comprises: (a) putting the test sample on a front surface of a substrate comprising a through hole; wherein the substrate comprises a cellulose film on the back surface thereof; the cellulose film has a thickness of not less than 0.5 micrometers and not more than 2 micrometers; and the through hole has a cross-sectional area of not less than 7.065 square micrometers and not more than 19.625 square micrometers; (b) leaving the test sample at rest; (c) observing a back surface of the film; and (d) determining that the test sample contains the phytopathogenic fungus, if a fungus is found on the back surface of the film.

1 Claim, 9 Drawing Sheets

--- Prior Art ---

METHOD FOR DETERMINING WHETHER OR NOT TEST SAMPLE CONTAINS PHYTOPATHOGENIC FUNGUS

CROSS-REFERENCES TO RELATED APPLICATIONS

This is a divisional of U.S. application Ser. No. 16/162,467, filed Oct. 17, 2018, which is a continuation of International Application No. PCT/JP2016/004417, with an international filing date of Sep. 30, 2016, which claims priority of Japanese Patent Application No. 2016-139916, filed on Jul. 15, 2016, the contents of which are hereby incorporated by reference.

BACKGROUND

1. Technical Field

The present invention relates to a method for determining whether or not a test sample contains a phytopathogenic fungus.

2. Description of the Related Art

Japanese Patent Application laid-open Publication No. 2005-287337A discloses a method for counting the number of mold cells in a specimen by the culture for a short time and capable of accurately counting the cell number. FIG. 12 shows a cross-sectional view of a microporous membrane supporting material used for the method disclosed therein. According to this method, the extended multiple pseudomycelia of a mold cell 13 cultured by a liquid culture or a mold cell 13 cultured on a microporous membrane 1 of a microporous membrane supporting material 4 are photographed and the shape, area and luminous intensity are recognized and analyzed by an image analytic means 10. The number of the mold cells 13 can be counted by the culture for a short time. The microporous membrane 1 is interposed between a pressing ring 2 and a base 3.

Paul F. Morris. et. al. "Chemotropic and Contact Responses of *Phytophthora sojae* Hyphae to Soybean Isoflavonoids and Artificial Substrates", Plant Physiol. (1998) 117: 1171-1178 discloses that hyphae of *Phytophthora sojae*, which is one of phytopathogenic oomycetes, penetrates the PET membrane having 3-micrometer pores.

SUMMARY

An object of the present invention is to provide a method for determining whether or not a test sample contains a phytopathogenic fungi selectively from two kinds of fungi of a phytopathogenic fungus and a non-phytopathogenic fungus.

The present invention provides a method for determining whether or not a test sample contains a phytopathogenic fungus, the method comprising:
(a) putting the test sample on a front surface of a substrate comprising a through hole;
wherein
the substrate comprises a cellulose film on the back surface thereof;
the cellulose film has a thickness of not less than 0.5 micrometers and not more than 2 micrometers; and
the through hole has a cross-sectional area of not less than 7.065 square micrometers and not more than 19.625 square micrometers;
(b) leaving the test sample at rest after the step (a);
(c) observing a back surface of the film after the step (b); and
(d) determining that the test sample contains the phytopathogenic fungus, if a fungus is found on the back surface of the film in the step (c).

The present invention provides a method for determining whether or not a test sample contains a phytopathogenic fungi selectively from two kinds of fungi of a phytopathogenic fungus and a non-phytopathogenic fungus.

DETAILED DESCRIPTION OF THE EMBODIMENT

Figure 1:
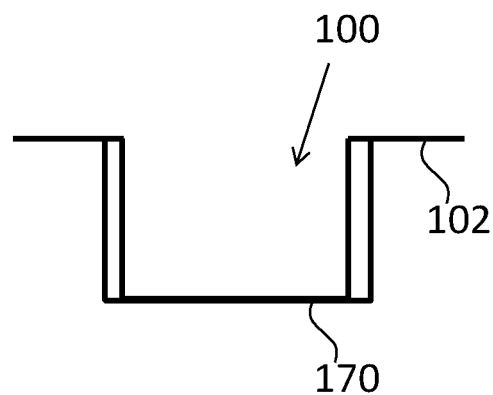
FIG. 1 shows a cross-sectional view of a first container 100.

First, a fungus will be described. Fungi are roughly divided into a phytopathogenic fungus and a non-phytopathogenic fungus. For example, the phytopathogenic fungus is a *Fusarium* genus, a *Pyricularia* genus, or a *Colletotrichum* genus. An example of the phytopathogenic fungus is *Fusarium oxysporum, Pyricularia grisea,* or *Colletotrichum gloeosporioides*. These phytopathogenic fungi cause root rot disease, blast, anthrax, or gray mold. These phytopathogenic fungi kill the plant. An example of the non-phytopathogenic fungus is *Saccharomyces cerevisiae, Penicillium chysogeum* or *Aspergillus oryzae*.

The term "phytopathogenic" means to have pathogenicity to plants. The term "non-phytopathogenic" means not to have pathogenicity to plants. Even if a fungus has pathogenicity, however, if the fungus has no pathogenicity to plants, the fungus is non-phytopathogenic. In other words, if a fungus does not have adverse effects on plants, the fungus is non-phytopathogenic. The prefix "non-" included in the term "non-phytopathogenic" does not modify "phyto". The prefix "non-" modifies "pathogenic".

Hereinafter, the embodiment of the present invention will be described in more detail with reference to the drawings.

(Step (a))

In the step (a), a test sample is put on a front surface of a substrate 170 comprising through holes 172. A cellulose film 104 is adhered to a back surface 170b of the substrate 170. In other words, a front surface 104a of the cellulose film 104 is in contact with the back surface 170b of the substrate 170.

In particular, as shown in FIG. 1, a container 100 is prepared. It is desirable that the container 100 comprises a flange 102 at the upper end thereof. The bottom surface of the container 100 is formed of the substrate 170.

Figure 2:
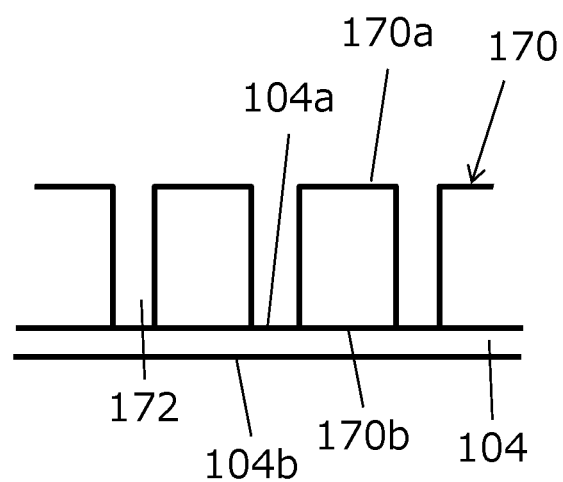
FIG. 2 shows a cross-sectional view of a substrate 170 comprising a cellulose film 104 on a back surface thereof.

As shown in FIG. 2, the substrate 170 comprises the cellulose film 104 on the back surface 170b thereof (i.e., on an outside surface of the bottom part of the container 100). The substrate 170 comprises the through hole 172 which penetrates from the front surface 170a to the back surface 170b of the substrate 170. The through hole 172 has a diameter of not less than 3 micrometers and not more than 5 micrometers. In other words, the through hole 172 has a cross-sectional area of not less than 7.065 square micrometers and not more than 19.625 square micrometers.

Figure 3:
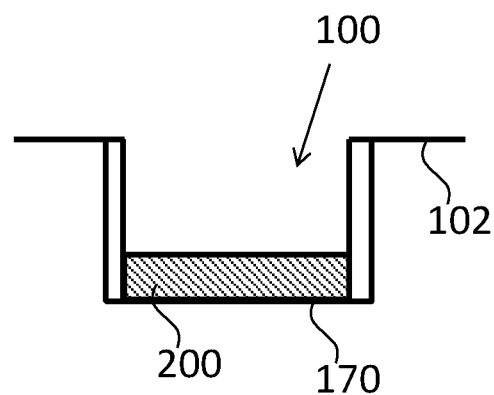
FIG. 3 shows a cross-sectional view of the first container 100 to which a test sample has been supplied.
Figure 4:
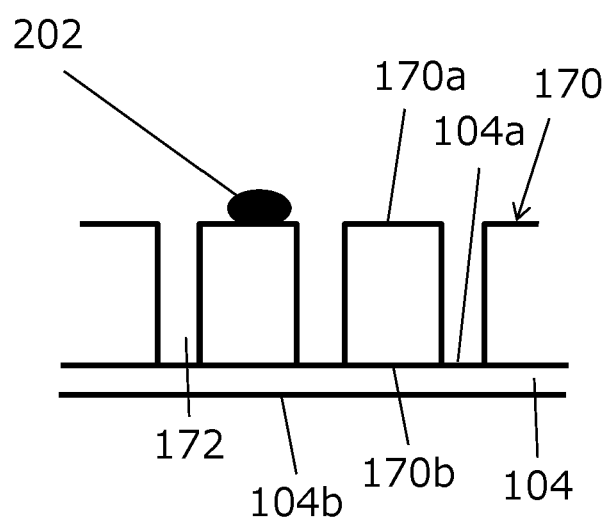
FIG. 4 shows a cross-sectional view of the substrate 170 having a front surface on which a phytopathogenic fungus has been put.

As shown in FIG. 3, a test sample 200 is supplied to an inside of this container 100. In this way, the test sample 200 is put on the front surface 170a of the substrate 170 (i.e., on an inside surface of the bottom part of the container 100). When the test sample 200 contains a phytopathogenic fungus 202, the phytopathogenic fungus 202 is put on the front surface 170a of the substrate 170, as shown in FIG. 4.

The test sample 200 is solid, liquid, or gaseous. It is desirable that the test sample 200 is solid or liquid. An example of the solid test sample 200 is soil or a crushed plant. Another example is an agricultural material such as vermiculite, rock wool or urethane. An example of the liquid test sample 200 is agricultural water, a solution used for hydroponic culture, a liquid used for washing a plant, a liquid extracted from a plant, a liquid used for washing an agricultural material, or a liquid used for washing clothing or shoes of a worker.

(Step (b))

In the step (b), the test sample 200 is left at rest for a certain incubation time after the step (a). Desirably, the test sample 200 is left at rest for 24 hours. In this way, the fungus is incubated. In other words, the incubation time is approximately 24 hours. Hereinafter, the importance of the thickness of the cellulose film 104 and the size of the through hole 172 will be described.

Figure 5:
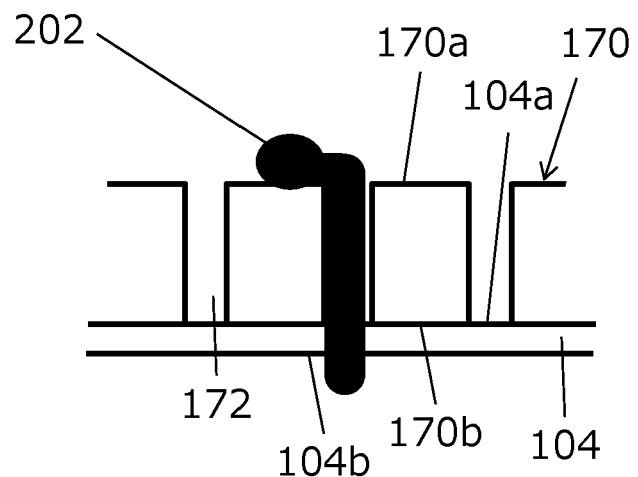
FIG. 5 is a cross-sectional view showing a state where the phytopathogenic fungus has penetrated a through hole 172 and the cellulose film 104.

In the step (b), various fungi contained in the test sample 200 are grown. As demonstrated in the experiments which will be described later, if both of the following requirements (I) and (II) are satisfied, the phytopathogenic fungus 202 grows up so as to penetrate both the through hole 172 and the cellulose film 104, as shown in FIG. 5. As a result, the phytopathogenic fungus 202 appears on a back surface 104b of the cellulose film 104.

Requirement (I): The cellulose film 104 has a thickness of not less than 0.5 micrometers and not more than 2 micrometers.

Requirement (II): The through hole 172 has a cross-sectional area of not less than 7.065 square micrometers and not more than 19.625 square micrometers.

If both of the above requirements (I) and (II) are satisfied, the non-phytopathogenic fungus hardly penetrates the cellulose film 104. As demonstrated in the comparative example 6C, at a maximum, the number of hyphae which penetrated cellulose film 104 is 31.9. For this reason, the non-phytopathogenic fungus hardly appears on the back surface 104b of the cellulose film 104. On the other hand, the phytopathogenic fungus 202 appears on the back surface 104b selectively. As demonstrated in the inventive example 3D, at a minimum, the number of hyphae which penetrated cellulose film 104 is 77.4. As just described, the phytopathogenic fungus 202 appears outside of the container 100 selectively.

In case where the cellulose film 104 has a thickness of more than 2 micrometers, neither the non-phytopathogenic fungus nor the phytopathogenic fungus penetrates the cellulose film 104. Therefore, in case where the cellulose film 104 has a thickness of more than 2 micrometers, the selectivity is lost. When the cellulose film 104 has a thickness of less than 0.5 micrometers (including a case where the cellulose film 104 is not provided), not only the non-phytopathogenic fungus but also the phytopathogenic fungus penetrates the cellulose film 104 (or are found on the back surface 170b of the substrate 170). Therefore, the selectivity is lost when the cellulose film 104 has a thickness of less than 0.5 micrometers.

In case where the through hole 172 has a cross-sectional area of less than 7.065 square micrometers (namely, a diameter of less than 3 micrometers), neither the non-phytopathogenic fungus nor the phytopathogenic fungus penetrates the cellulose film 104. On the other hand, the through hole 172 has a cross-sectional area of more than 19.625 square micrometers (namely, a diameter of more than 5 micrometers), the number of hyphae which penetrated cellulose film 104 tends to be lowered, compared to the case where the through hole 172 has a cross-sectional area of 19.625 square micrometers (namely, a diameter of 5 micrometers).

The cellulose film 104 is stretched tautly on the back surface 170b of the substrate 170. In this way, the substrate 170 supports the cellulose film 104.

As shown in FIG. 2, it is desirable that the substrate 170 has a plurality of through holes 172. The thickness of the substrate 170 is not limited; however, as one example, it is desirable that the substrate 170 has a thickness of not less than 1 micrometer and not more than 500 micrometers. The cellulose film 104 is significantly thin. However, if the cellulose film 104 is arranged on the substrate 170, it is easy to handle the cellulose film 104.

A culture medium may be supplied to the test sample 200 to accelerate the incubation of the fungus. In particular, a culture medium may be supplied to the inside of the container 100 containing the test sample 200. It is desirable that the culture medium is liquid. The culture medium may be supplied in the step (b). Alternatively, the culture medium may be supplied prior to the step (b). In other words, the culture medium may be supplied in the step (a). The culture medium may be supplied to the inside of the container 100 prior to the step (a).

Figure 6:
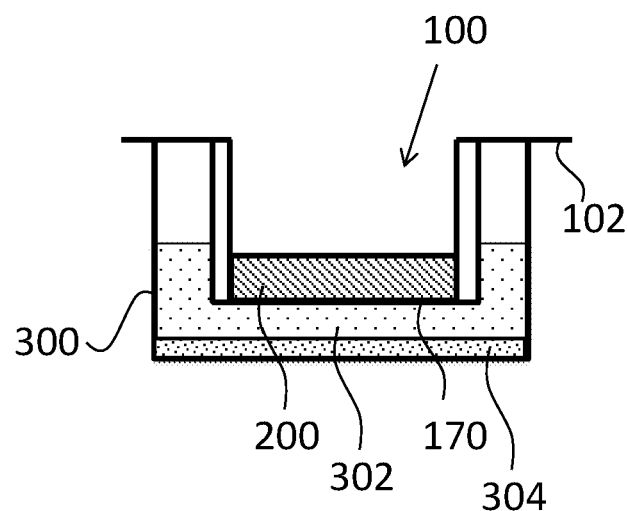
FIG. 6 shows a cross-sectional view of one example of a method for accelerating an incubation of the fungus.

FIG. 6 shows another method for accelerating the incubation of the fungus. As shown in FIG. 6, it is desirable that the back surface 104b of the cellulose film 104 is in contact with a liquid culture medium 302. First, a second container 300 having the liquid culture medium 302 therein is prepared. Hereinafter, the container 100 is referred to as "first container 100" to distinguish it from the second container 300. The first container 100 is stacked on the second container 300 in such a manner that the lower surface of the flange 102 is in contact with the upper end of the second container 300. In other words, the first container 100 is supported by the upper end of the second container 300. In this way, the liquid culture medium 302 is sandwiched between the back surface 104b of the cellulose film 104 and the bottom surface of the second container 300.

Alternatively, after the first container 100 is stacked on the second container 300, the liquid culture medium 302 may be supplied between the back surface 104b of the cellulose film 104 and the bottom surface of the second container 300.

In place of the liquid culture medium 302, a viscous solid culture medium may also be used. As shown in FIG. 6, both of a solid culture medium 304 and the liquid culture medium 302 may be used. In this case, the liquid culture medium 302 is sandwiched between the solid culture medium 304 and the cellulose film 104. As shown in FIG. 5, the incubation of the phytopathogenic fungus which has appeared on the back surface 104b is accelerated by at least one of the liquid culture medium 302 and the solid culture medium 304.

(Step (c))

In the step (c), the back surface 104b of the cellulose film 104 is observed after the step (b). It is desirable that the back surface 104b is observed using an optical microscope.

The phytopathogenic fungus 202 appears on the back surface 104b of the cellulose film 104, as described in the step (b). On the other hand, the non-phytopathogenic fungus does not appear on the back surface 104b of the cellulose film 104. In this way, in the present invention, the phytopathogenic fungus 202 appears on the back surface 104b of the cellulose film 104 selectively.

In other words, the phytopathogenic fungus 202 penetrates the cellulose film 104, whereas the non-phytopathogenic fungus does not penetrate the cellulose film 104. For this reason, the non-phytopathogenic fungus does not appear on the back surface 104b of the cellulose film 104. In this way, the phytopathogenic fungus 202 appears on the back surface 104b selectively. In other words, the phytopathogenic fungus 202 appears outside of the first container 100 selectively.

In the step (c), it is observed whether or not the phytopathogenic fungus 202 appears on the back surface 104b of the cellulose film 104.

In particular, whether or not the phytopathogenic fungus 202 appears on the back surface 104b of the cellulose film 104 is observed as below.

Figure 8:
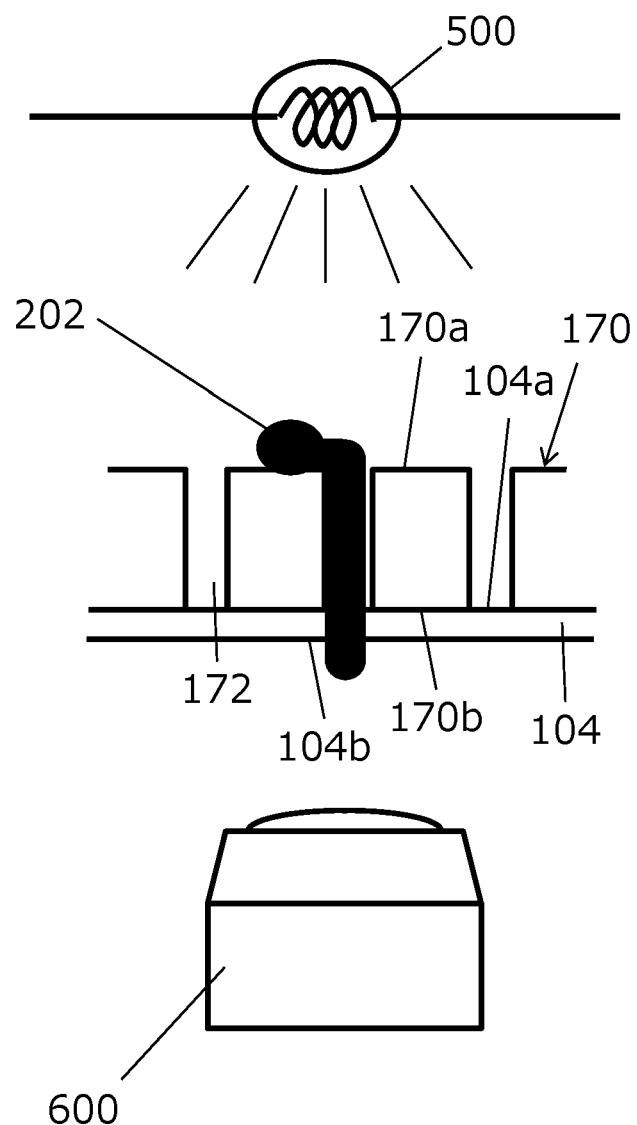
FIG. 8 is a cross-sectional view showing how to observe the fungus from the back surface of the cellulose film 104.

As shown in FIG. 8, while the cellulose film 104 is irradiated with light emitted from a light source 500 arranged above the front surface 170a of the substrate 170, the phytopathogenic fungus 202 is observed optically using a microscope 600 arranged below the back surface 104b of the cellulose film 104.

Figure 7:
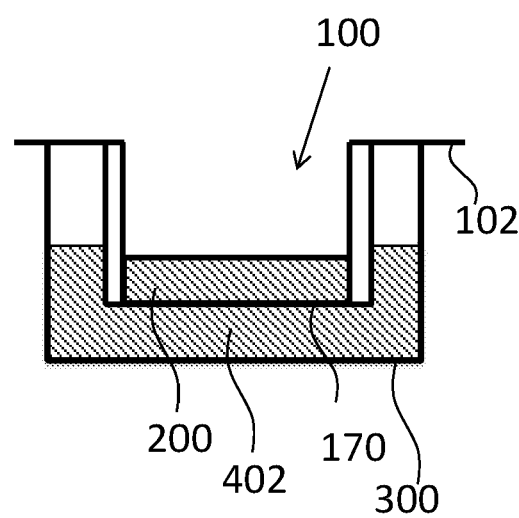
FIG. 7 shows a cross-sectional view, subsequently to FIG. 6, of one example of a method for accelerating the incubation of the fungus.

The liquid culture medium 302 and the solid culture medium 304 are removed from the second container 300. Then, a fluorescent agent having fungus combining ability is added to the inside of the second container 300. Hereinafter, such a fluorescent agent is referred to as "fungus fluorescent agent". The reference number of the fungus fluorescent agent is 402. Then, as shown in FIG. 7, the first container 100 is stacked on the second container 300 having the fungus fluorescent agent 402 therein. Alternatively, the fungus fluorescent agent 402 may be supplied between the back surface 104b of the cellulose film 104 and the bottom surface of the second container 300 after the first container 100 is stacked on the second container 300.

A part of the phytopathogenic fungus 202 which has appeared on the back surface 104b of the cellulose film 104 may be dyed with the fungus fluorescent agent 402. Since the first container 100 is separated from the second container 300 by the cellulose film 104, the fungus fluorescent agent 402 does not spread into the first container 100. For this reason, the non-phytopathogenic fungus contained in the first container 100 is not dyed with the fungus fluorescent agent 402.

Figure 9:
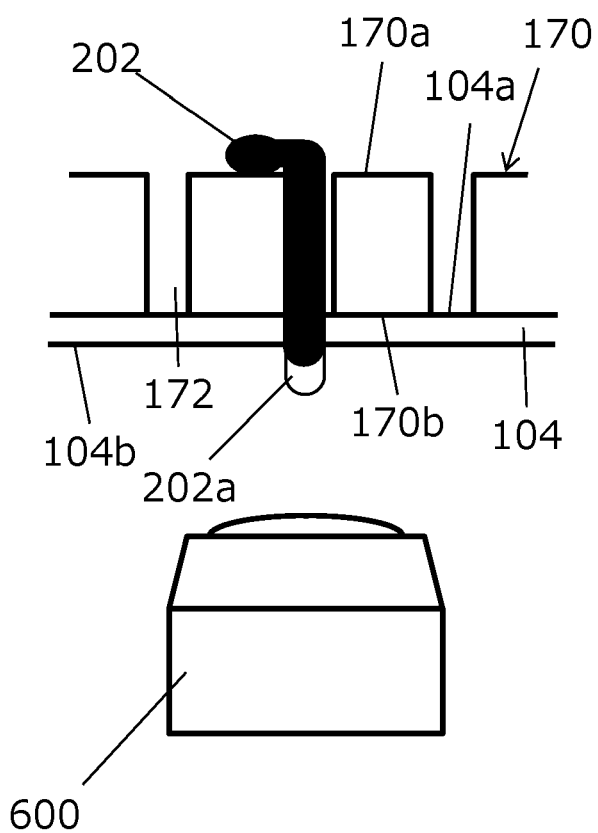
FIG. 9 is a cross-sectional view showing how to observe the fungus from the back surface of the cellulose film 104.
Figure 10:
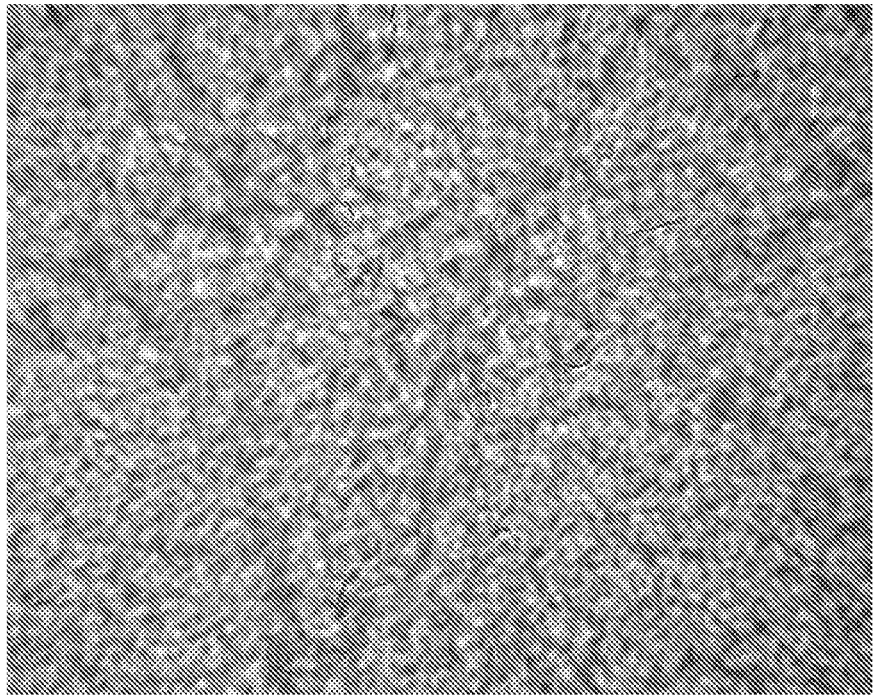
FIG. 10 is a microscope photograph of the back surface of the cellulose film 104 in an inventive example 1A.

As shown in FIG. 9, the phytopathogenic fungus 202 dyed with the fungus fluorescent agent 402 is observed using the epifluorescence microscope 600 located under the back surface 104b of the cellulose film 104. Needless to say, the phytopathogenic fungus 202 may be observed without using the fungus fluorescent agent.

(Step (d))

In the step (d), it is determined that the test sample contains a phytopathogenic fungus, if a fungus is found on the back surface 104b of the cellulose film 104 in the step (c). Needless to say, it is determined that the test sample does not contain a phytopathogenic fungus, if a fungus is not found on the back surface 104b of the cellulose film 104 in the step (c).

EXAMPLES

The present invention will be described in more detail with reference to the following examples.

(Incubation of *Fusarium oxysporum*)

*Fusarium oxysporum*, one of phytopathogenic fungi, was inoculated on a potato dextrose agar culture medium. Then, the culture medium was left at rest at a temperature of 25 degrees Celsius for one week. *Fusarium oxysporum* was given by an associate professor, Mr. Shimizu, who belongs to Graduate School of Applied Biological Sciences and Faculty of Applied Biological Sciences, Gifu University.

Then, a part including ends of hyphae was cut together with the culture medium at a size of 1 centimeter×1 centimeter. The cut part was immersed in pure water disposed on a 12-well plate. Each of the pure water has a volume of 1 milliliter.

The water contained in the 12-well plate was observed using an optical microscope. As a result, the present inventors confirmed that spores of *Fusarium oxysporum* were released in the water disposed on the 12-well plate. In this way, an aqueous solution containing *Fusarium oxysporum* was provided. Hereinafter, this aqueous solution is referred to as "phytopathogenic fungus aqueous solution".

(Preparation of Culture Medium)

A potato dextrose culture medium having a volume of 650 microliters was added as the liquid culture medium 302 to the second container 300. In this way, the second container 300 containing the liquid culture medium 302 was prepared.

Experiment 1

The experiment 1 is composed of inventive examples 1A-1D, and comparative examples 1E-1L.

Inventive Example 1A

The first container 100 shown in FIG. 1 was prepared as below.

First, cellulose (available from SIGMA-ALDRICH Co. LLC, trade name: Avicel PH-101) was dissolved in an ionic liquid to prepare a cellulose solution having a concentration of 2%. The ionic liquid was 1-butyl-3-methyl imidazolium chloride (available from SIGMA-ALDRICH Co. LLC).

The cellulose solution was warmed to 60 degrees Celsius. Then, the cellulose solution was applied by a spin coat method for thirty seconds at a rotation speed of 2,000 rpm onto a back surface of a container having a polyethylene terephthalate film on the bottom surface thereof (available from Merck KGaA, trade name: Millicell PISP 12R 48). The polyethylene terephthalate film was served as the substrate 170. The polyethylene terephthalate film randomly had a plurality of through holes 172 each having a diameter of three micrometers. In this way, the cellulose film 104 having a thickness of 2.0 micrometers was formed on the back surface of the polyethylene terephthalate film. According to Merck KGaA, the diameter of the through-hole 172 may have a margin of error of approximately ±10%.

The container was left at rest in ethanol at room temperature for 12 hours. In this way, 1-butyl-3-methyl imidazolium chloride was replaced with ethanol. In other words, 1-butyl-3-methyl imidazolium chloride was removed from the cellulose film 104.

Finally, the container was dried in a vacuum desiccator. In this way, the first container 100 shown in FIG. 1 was obtained. In FIG. 1, note that the polyethylene terephthalate film serving as the substrate 170 is not illustrated.

Then, as shown in FIG. 6, the first container 100 was stacked on the second container 300. The back surface 104b of the cellulose film 104 was in contact with the liquid culture medium 302. Subsequently, water having a volume of 200 microliters was added to the inside of the first container 100. Furthermore, the phytopathogenic fungus aqueous solution containing 200 spores of *Fusarium oxysporum* was added to the inside of the first container 100.

The first container 100 was left at rest at a temperature of 25 degrees Celsius for 24 hours. In other words, in the inventive example 1A, the incubation time was 24 hours.

The number of the hyphae of *Fusarium oxysporum* which appeared on the back surface 104*b* of the cellulose film 104 was counted visually with an optical microscope. The inventive example 1A was repeated fifteen times. As a result, the mean value of the number of the hyphae of *Fusarium oxysporum* which appeared on the back surface 104*b* was 44.9. FIG. 10 is a microscope photograph of the back surface of the cellulose film 104 in the inventive example 1A.

Inventive Example 1B

In the inventive example 1B, an experiment similar to the inventive example 1A was conducted, except that each of the through holes 172 had a diameter of 5 micrometers. The container having a bottom surface comprising the through holes each having a diameter of 5 micrometers was available from Merck KGaA as a trade name: Millicell PIMP 12R 48.

Inventive Example 1C

In the inventive example 1C, an experiment similar to the inventive example 1A was conducted, except that the cellulose solution had a concentration of 1.0% and that the cellulose film 104 had a thickness of 0.5 micrometers.

Inventive Example 1D

In the inventive example 1D, an experiment similar to the inventive example 1A was conducted, except that the cellulose solution had a concentration of 1.0%, that the cellulose film 104 had a thickness of 0.5 micrometers, and that each of the through holes 172 had a diameter of 5 micrometers.

Comparative Example 1E

In the comparative example 1E, an experiment similar to the inventive example 1A was conducted, except that each of the through holes 172 had a diameter of 1 micrometer. The container having a bottom surface comprising the through holes each having a diameter of 1 micrometer was available from Merck KGaA as a trade name: Millicell PIRP 12R 48.

Comparative Example 1F

In the comparative example 1F, an experiment similar to the inventive example 1A was conducted, except that each of the through holes 172 had a diameter of 8 micrometers. The container having a bottom surface comprising the through holes each having a diameter of 8 micrometers was available from Merck KGaA as a trade name: Millicell PIEP 12R 48.

Comparative Example 1G

In the comparative example 1G, an experiment similar to the inventive example 1A was conducted, except that the cellulose film 104 had a thickness of 0.5 micrometers (namely, the cellulose solution had a concentration of 1.0%) and that the each of the through holes 172 had a diameter of 1 micrometer.

Comparative Example 1H

In the comparative example 1H, an experiment similar to the inventive example 1A was conducted, except that the cellulose film 104 had a thickness of 0.5 micrometers (namely, the cellulose solution had a concentration of 1.0%) and that the each of the through holes 172 had a diameter of 8 micrometers.

Comparative Example 1I

In the comparative example 1I, an experiment similar to the inventive example 1A was conducted, except that the cellulose film 104 was not formed (namely, the cellulose film 104 had a thickness of 0 micrometers) and that the each of the through holes 172 had a diameter of 1 micrometer.

Comparative Example 1J

In the comparative example 1J, an experiment similar to the inventive example 1A was conducted, except that the cellulose film 104 was not formed (namely, the cellulose film 104 had a thickness of 0 micrometers).

Comparative Example 1K

In the comparative example 1K, an experiment similar to the inventive example 1A was conducted, except that the cellulose film 104 was not formed (namely, the cellulose film 104 had a thickness of 0 micrometers) and that the each of the through holes 172 had a diameter of 5 micrometers.

Comparative Example 1L

In the comparative example 1L, an experiment similar to the inventive example 1A was conducted, except that the cellulose film 104 was not formed (namely, the cellulose film 104 had a thickness of 0 micrometers) and that the each of the through holes 172 had a diameter of 8 micrometers.

Experiment 2

In the experiment 2, a non-phytopathogenic fungus aqueous solution containing spores of *Saccharomyces cerevisiae* was used in place of the phytopathogenic fungus aqueous solution containing spores of *Fusarium oxysporum*. Unlike

Figure 11:
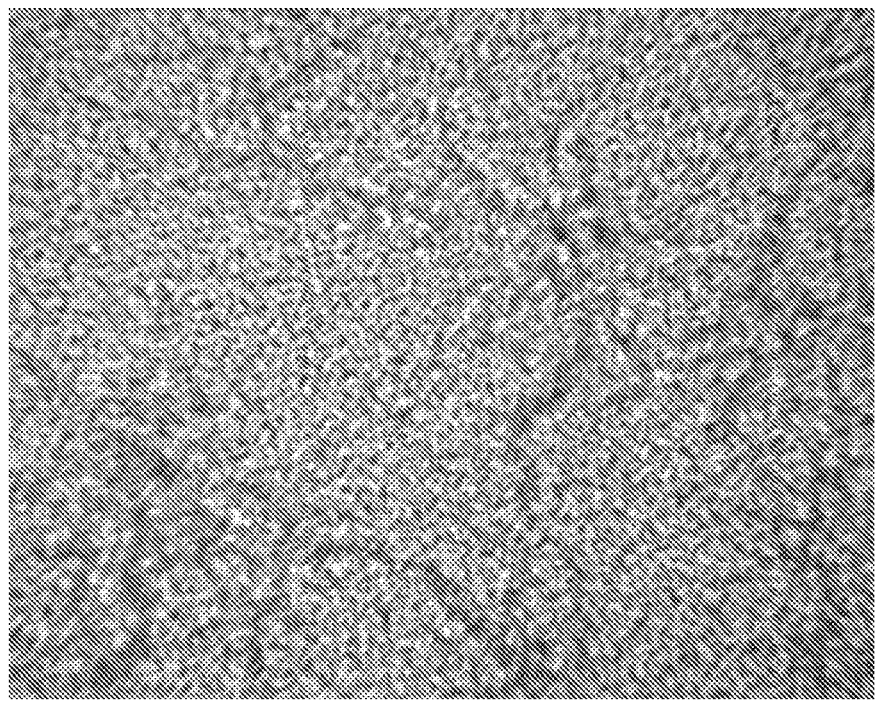
FIG. 11 is a microscope photograph of the back surface of the cellulose film 104 in a comparative example 2A.
Figure 12:
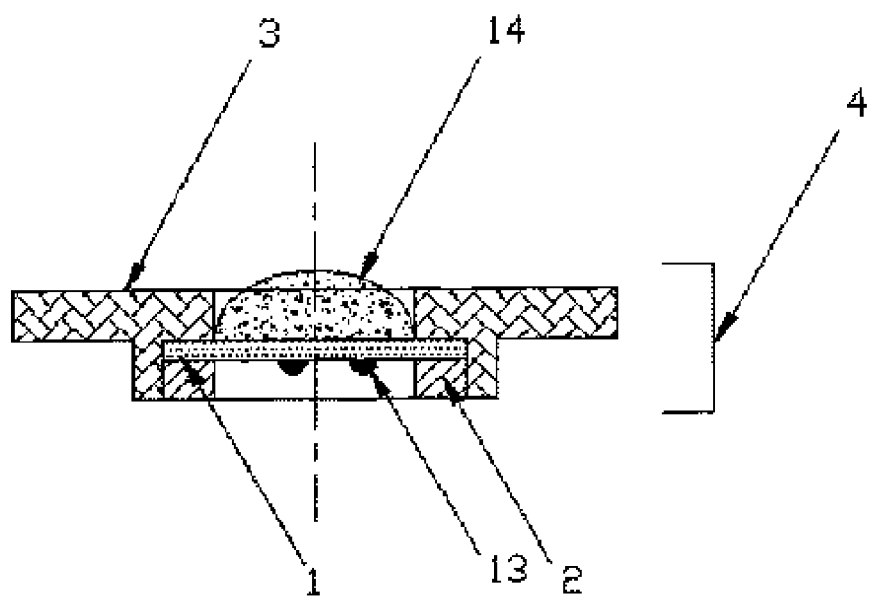
FIG. 12 shows a cross-sectional view of a microporous membrane supporting material used for a method for counting the number of mold cells disclosed in Japanese Patent Application laid-open Publication No. 2005-287337A.

*Fusarium oxysporum, Saccharomyces cerevisiae* is one kind of non-phytopathogenic fungus. A non-phytopathogenic fungus aqueous solution containing spores of *Saccharomyces cerevisiae* was prepared similarly to the case of the phytopathogenic fungus aqueous solution containing spores of *Fusarium oxysporum*. The experiment 2 is composed of comparative examples 2A-2L. The comparative examples 2A-2L were similar to the inventive example 1A—the comparative example 1L, except of using another fungus. FIG. 11 is a microscope photograph of the back surface of the cellulose film 104 in the comparative example 2A.

Experiment 3

In the experiment 3, a non-phytopathogenic fungus aqueous solution containing spores of *Pyricularia grisea* was used in place of the phytopathogenic fungus aqueous solution containing spores of *Fusarium oxysporum*. Similarly to *Fusarium oxysporum*, *Pyricularia grisea* is one kind of phytopathogenic fungus. A phytopathogenic fungus aqueous solution containing spores of *Pyricularia grisea* was prepared as below.

(Incubation of *Pyricularia griseas*)

*Pyricularia grisea*, one of phytopathogenic fungi, was inoculated on an oatmeal agar culture medium containing 2% sucrose. Then, the culture medium was left at rest at a temperature of 25 degrees Celsius for one week. Subsequently, the culture medium was left at rest for four days under near-ultraviolet radiation.

Then, a part including ends of hyphae was cut together with the culture medium at a size of 1 centimeter×1 centimeter. The cut part was immersed in pure water disposed on a 12-well plate. Each of the pure water has a volume of 1 milliliter.

The water contained in the 12-well plate was observed using an optical microscope. As a result, the present inventors confirmed that spores of *Pyricularia grisea* were released in the water disposed on the 12-well plate. In this way, an aqueous solution containing *Pyricularia grisea* was provided.

The experiment 3 is composed of the inventive examples 3A-3D and the comparative examples 3E-3L. The inventive examples 3A-3D and the comparative examples 3E-3L were similar to the inventive examples 1A-1D and the comparative examples 1E-1L, respectively, except of using another fungus.

Experiment 4

In the experiment 4, a non-phytopathogenic fungus aqueous solution containing spores of *Colletotrichum gloeosporioides* was used in place of the phytopathogenic fungus aqueous solution containing spores of *Fusarium oxysporum*. Similarly to *Fusarium oxysporum*, *Colletotrichum gloeosporioides* is one kind of phytopathogenic fungus. A phytopathogenic fungus aqueous solution containing spores of *Colletotrichum gloeosporioides* was prepared similarly to the case of the phytopathogenic fungus aqueous solution containing spores of *Fusarium oxysporum*. The experiment 4 is composed of the inventive examples 4A-4D and the comparative examples 4E-4L. The inventive examples 4A-4D and the comparative examples 4E-4L were similar to the inventive examples 1A-1D and the comparative examples 1E-1L, respectively, except of using another fungus.

Experiment 5

In the experiment 5, a non-phytopathogenic fungus aqueous solution containing spores of *Penicillium chysogeum* was used in place of the phytopathogenic fungus aqueous solution containing spores of *Fusarium oxysporum*. Unlike *Fusarium oxysporum*, *Penicillium chysogeum* is one kind of non-phytopathogenic fungus. A non-phytopathogenic fungus aqueous solution containing spores of *Penicillium chysogeum* was prepared similarly to the case of the phytopathogenic fungus aqueous solution containing spores of *Fusarium oxysporum*. The experiment 5 is composed of comparative examples 5A-5L. The comparative examples 5A-5L were similar to the inventive example 1A—the comparative example 1L, except of using another fungus.

Experiment 6

In the experiment 6, a non-phytopathogenic fungus aqueous solution containing spores of *Aspergillus oryzae* was used in place of the phytopathogenic fungus aqueous solution containing spores of *Fusarium oxysporum*. Unlike *Fusarium oxysporum*, *Aspergillus oryzae* is one kind of non-phytopathogenic fungus. A non-phytopathogenic fungus aqueous solution containing spores of *Aspergillus oryzae* was prepared similarly to the case of the phytopathogenic fungus aqueous solution containing spores of *Fusarium oxysporum*. The experiment 6 is composed of comparative examples 6A-6L. The comparative examples 6A-6L were similar to the inventive example 1A—the comparative example 1L, except of using another fungus.

The following Table 1-Table 6 show the number of the hyphae which penetrated the cellulose film 104 in the experiments.

TABLE 1

|  | Film thickness (μm) | Diameter of Through hole (μm) | Name of Fungus | Number of hyphae which penetrated cellulose film 104 |
|---|---|---|---|---|
| C. example 1E | 2 | 1 | *Fusarium oxysporum* (phytopathogenic) | 0 |
| I. example 1A |  | 3 |  | 44.9 |
| I. example 1B |  | 5 |  | 42.8 |
| C. example 1F |  | 8 |  | 16.3 |
| C. example 1G | 0.5 | 1 |  | 0.5 |
| I. example 1C |  | 3 |  | 106.5 |
| I. example 1D |  | 5 |  | 94.1 |
| C. example 1H |  | 8 |  | 125.4 |
| C. example 1I | 0 | 1 |  | 0.3 |
| C. example 1J |  | 3 |  | 125.3 |
| C. example 1K |  | 5 |  | 33.3 |
| C. example 1L |  | 8 |  | 15 |

Incubation time: 24 hours

C.: Comparative

I.: Inventive

TABLE 2

|  | Film thickness (μm) | Diameter of Through hole (μm) | Name of Fungus | Number of hyphae which penetrated cellulose film 104 |
| --- | --- | --- | --- | --- |
| C. example 2E | 2 | 1 | Saccharomyces cerevisiae (non-phytopathogenic) | 0 |
| C. example 2A |  | 3 |  | 0 |
| C. example 2B |  | 5 |  | 0 |
| C. example 2F |  | 8 |  | 0 |
| C. example 2G | 0.5 | 1 |  | 0 |
| C. example 2C |  | 3 |  | 0 |
| C. example 2D |  | 5 |  | 0 |
| C. example 2H |  | 8 |  | 0 |
| C. example 2I | 0 | 1 |  | 0 |
| C. example 2J |  | 3 |  | 0 |
| C. example 2K |  | 5 |  | 0 |
| C. example 2L |  | 8 |  | 0 |

Incubation time: 24 hours
C.: Comparative
I.: Inventive

TABLE 3

|  | Film thickness (μm) | Diameter of Through hole (μm) | Name of Fungus | Number of hyphae which penetrated cellulose film 104 |
| --- | --- | --- | --- | --- |
| C. example 3E | 2 | 1 | Pyricularia grisea (phytopathogenic) | 2 |
| I. example 3A |  | 3 |  | 64.1 |
| I. example 3B |  | 5 |  | 53 |
| C. example 3F |  | 8 |  | 84.9 |
| C. example 3G | 0.5 | 1 |  | 8 |
| I. example 3C |  | 3 |  | 85.3 |
| I. example 3D |  | 5 |  | 77.4 |
| C. example 3H |  | 8 |  | 99.4 |
| C. example 3I | 0 | 1 |  | 4 |
| C. example 3J |  | 3 |  | 11 |
| C. example 3K |  | 5 |  | 15.7 |
| C. example 3L |  | 8 |  | 7.7 |

Incubation time: 24 hours
C.: Comparative
I.: Inventive

TABLE 4

|  | Film thickness (μm) | Diameter of Through hole (μm) | Name of Fungus | Number of hyphae which penetrated cellulose film 104 |
| --- | --- | --- | --- | --- |
| C. example 4E | 2 | 1 | Colletotrichum gloeosporioides (phytopathogenic) | 0 |
| I. example 4A |  | 3 |  | 83.3 |
| I. example 4B |  | 5 |  | 55.2 |
| C. example 4F |  | 8 |  | 8.7 |
| C. example 4G | 0.5 | 1 |  | 4 |
| I. example 4C |  | 3 |  | 326 |
| I. example 4D |  | 5 |  | 449 |
| C. example 4H |  | 8 |  | 165.3 |
| C. example 4I | 0 | 1 |  | 1.3 |
| C. example 4J |  | 3 |  | 182.7 |
| C. example 4K |  | 5 |  | 91.3 |
| C. example 4L |  | 8 |  | 62.7 |

Incubation time: 24 hours
C.: Comparative
I.: Inventive

TABLE 5

| | Film thickness (μm) | Diameter of Through hole (μm) | Name of Fungus | Number of hyphae which penetrated cellulose film 104 |
|---|---|---|---|---|
| C. example 5E | 2 | 1 | Penicillium chysogeum (non-phytopathogenic) | 0 |
| C. example 5A | | 3 | | 0 |
| C. example 5B | | 5 | | 0 |
| C. example 5F | | 8 | | 0 |
| C. example 5G | 0.5 | 1 | | 0 |
| C. example 5C | | 3 | | 0 |
| C. example 5D | | 5 | | 0 |
| C. example 5H | | 8 | | 6.8 |
| C. example 5I | 0 | 1 | | 0 |
| C. example 5J | | 3 | | 10 |
| C. example 5K | | 5 | | 11.7 |
| C. example 5L | | 8 | | 4.3 |

Incubation time: 24 hours
C.: Comparative
I.: Inventive

TABLE 6

| C.: Comparative I.: Inventive | Film thickness (μm) | Diameter of Through hole (μm) | Name of Fungus | Number of hyphae which penetrated cellulose film 104 |
|---|---|---|---|---|
| C. example 6E | 2 | 1 | Aspergillus oryzae (non-phytopathogenic) | 0 |
| C. example 6A | | 3 | | 0 |
| C. example 6B | | 5 | | 2.7 |
| C. example 6F | | 8 | | 1.6 |
| C. example 6G | 0.5 | 1 | | 1 |
| C. example 6C | | 3 | | 31.9 |
| C. example 6D | | 5 | | 18.8 |
| C. example 6H | | 8 | | 18.9 |
| C. example 6I | 0 | 1 | | 1 |
| C. example 6J | | 3 | | 48 |
| C. example 6K | | 5 | | 56 |
| C. example 6L | | 8 | | 23.7 |

Incubation time: 24 hours
C.: Comparative
I.: Inventive

As is clear from Table 1-Table 6, when both of the following requirements (I) and (II) are satisfied, the phytopathogenic fungus appears on the back surface 104b of the cellulose film 104 selectively. In other words, the phytopathogenic fungus 202 appears outside of the container 100 selectively.

Requirement (I): The cellulose film 104 has a thickness of not less than 0.5 micrometers and not more than 2 micrometers.

Requirement (II): The through hole 172 has a diameter of not less than 3 micrometers and not more than 5 micrometers.

As demonstrated in the inventive example 3D in which both of the requirements (I) and (II) are satisfied, the number of hyphae which penetrated cellulose film 104 is 77.4 at a minimum. On the other hand, as long as both of the requirements (I) and (II) are satisfied, the non-phytopathogenic fungus hardly appears the back surface 104b of the cellulose film 104. As demonstrated in the comparative example 6C in which both of the requirements (I) and (II) are satisfied, the number of hyphae which penetrated cellulose film 104 is 31.9 at a maximum.

INDUSTRIAL APPLICABILITY

The present invention can be used to determine easily whether or not a test sample such as agricultural water or soil contains a phytopathogenic fungus.

REFERENCE SIGNS LIST

100 First container
  102 Flange
  104 Cellulose film
    104a Front surface
    104b Back surface
  170 Substrate
    170a Front surface
    170b Back surface
200 Test sample
  202 Phytopathogenic fungus
    202a Part of Phytopathogenic fungus
  300 Second container
    302 Liquid culture medium
    304 Solid culture medium
  402 Fluorescent agent having fungus combining ability
  500 Light source
  600 Microscope

The invention claimed is:

1. A container for testing a phytopathogenic fungus, wherein
the container has a bottom part,
the bottom part is formed of a substrate,
a cellulose film is adhered on an outside surface of the bottom part,
the cellulose film has a thickness of not less than 0.5 micrometers and not more than 2 micrometers,
the substrate comprises a through hole,
the through hole has a cross-sectional area of not less than 7.065 square micrometers and not more than 19.625 square micrometers, and
one end of the through hole is fully covered by the cellulose film.

* * * * *